US00PP25198P3

(12) United States Plant Patent
Schoone

(10) Patent No.: US PP25,198 P3
(45) Date of Patent: Dec. 30, 2014

(54) ***PHALAENOPSIS* ORCHID PLANT NAMED 'MIRACULOUS'**

(50) Latin Name: ***Phalaenopsis* hybrid**
Varietal Denomination: Miraculous

(71) Applicant: Floricultura, Heemskerk (NL)

(72) Inventor: René Schoone, Assendelft (NL)

(73) Assignee: Floricultura, Heemskerk (NL)

( * ) Notice: Subject to any disclaimer, the term of this patent is extended or adjusted under 35 U.S.C. 154(b) by 113 days.

(21) Appl. No.: 13/573,558

(22) Filed: Sep. 25, 2012

(65) Prior Publication Data

US 2013/0081169 P1 Mar. 28, 2013

Related U.S. Application Data

(60) Provisional application No. 61/540,412, filed on Sep. 28, 2011.

(30) Foreign Application Priority Data

Sep. 30, 2011 (NL) ..... PBR OPS840

(51) Int. Cl.
*A01H 5/00* (2006.01)
*A01H 5/02* (2006.01)

(52) U.S. Cl.
CPC ..... *A01H 5/02* (2013.01)
USPC ..... Plt./311

(58) Field of Classification Search
USPC ..... Plt./311
See application file for complete search history.

(56) References Cited

U.S. PATENT DOCUMENTS

PP10,682 P * 11/1998 Plate ..... Plt./311
PP20,199 P3 * 8/2009 Lin ..... Plt./311

* cited by examiner

*Primary Examiner* — Susan McCormick Ewoldt
(74) *Attorney, Agent, or Firm* — Foley & Lardner LLP; Sunit Talapatra

(57) ABSTRACT

A new and distinct *Phalaenopsis* plant named 'Miraculous' particularly characterized by flowers which are white with purple stripes; the labellum is purple with some white and yellow; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis* hybrid.

Variety denomination: 'Miraculous'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Miraculous'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'Miraculous' is a product of a controlled breeding program conducted by the inventors, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Miraculous' originated from a cross made by the inventor in 1999 in Strengweg, Heemskerk, The Netherlands. The female or seed parent is the *Phalaenopsis* cultivar designated 'Sun Prince', unpatented. The male or pollen parent is the *Phalaenopsis* cultivar designated 'Super Stupid', unpatented. The new *Phalaenopsis* 'Miraculous' was discovered and selected by the inventor as a single flowering plant within the progeny of the stated cross in a controlled environment in 2006 in Strengweg, Heemskerk, The Netherlands.

Asexual reproduction of the new *Phalaenopsis* cultivar by tissue culture was first performed in July, 2007 in Cieweg 13, Heemskerk, The Netherlands, and has demonstrated that the combination of characteristics as herein disclosed for the new cultivar are firmly fixed and retained through successive generations of asexual reproduction. The new cultivar asexually reproduces true-to-type.

BRIEF DESCRIPTION OF THE INVENTION

The following traits have been repeatedly observed and are determined to be unique characteristics of 'Miraculous', which in combination distinguish this *Phalaenopsis* as a new and distinct cultivar:

1. flowers which are white with purple stripes; the labellum is purple with some white and yellow;
2. plant produces more than one inflorescence;
3. plants may be propagated economically and uniformly using tissue culture;
4. inflorescences are long and sturdy; and
5. relatively short, dark-green foliage.

In comparison with the parental cultivars of 'Miraculous', the female parent 'Sun Prince' has white colored flowers with purple/violet stripes, a red/purple labellum and a purple column. The male parent 'Super Stupid' has white colored flowers with purple spots, a red labellum and a white column, whereas the flowers of 'Miraculous' are white with red/purple stripes and spots, a purple labellum and a purple column.

Presently, the commercial cultivar to which 'Miraculous' can be meaningfully compared is 'Sunrise Crystal' (Patented, U.S. Pat. No. 20,199). The flowers of 'Sunrise Crystal' are white and slightly yellow, with purple stripes, the labellum is red/purple and the lateral sepals are light yellow. Whereas the flowers of 'Miraculous' are white and slightly pink, with red/purple stripes, the labellum is purple and the lateral sepals are white.

BRIEF DESCRIPTION OF THE PHOTOGRAPHS

The accompanying photographs illustrate the overall appearance of the new *Phalaenopsis* 'Miraculous' showing the colors as true as is reasonably possible with colored reproductions of this type. Colors in the photographs may differ slightly from the color values cited in the detailed botanical description, which accurately describe the color of 'Miraculous'.

DETAILED BOTANICAL DESCRIPTION

Figure 1:
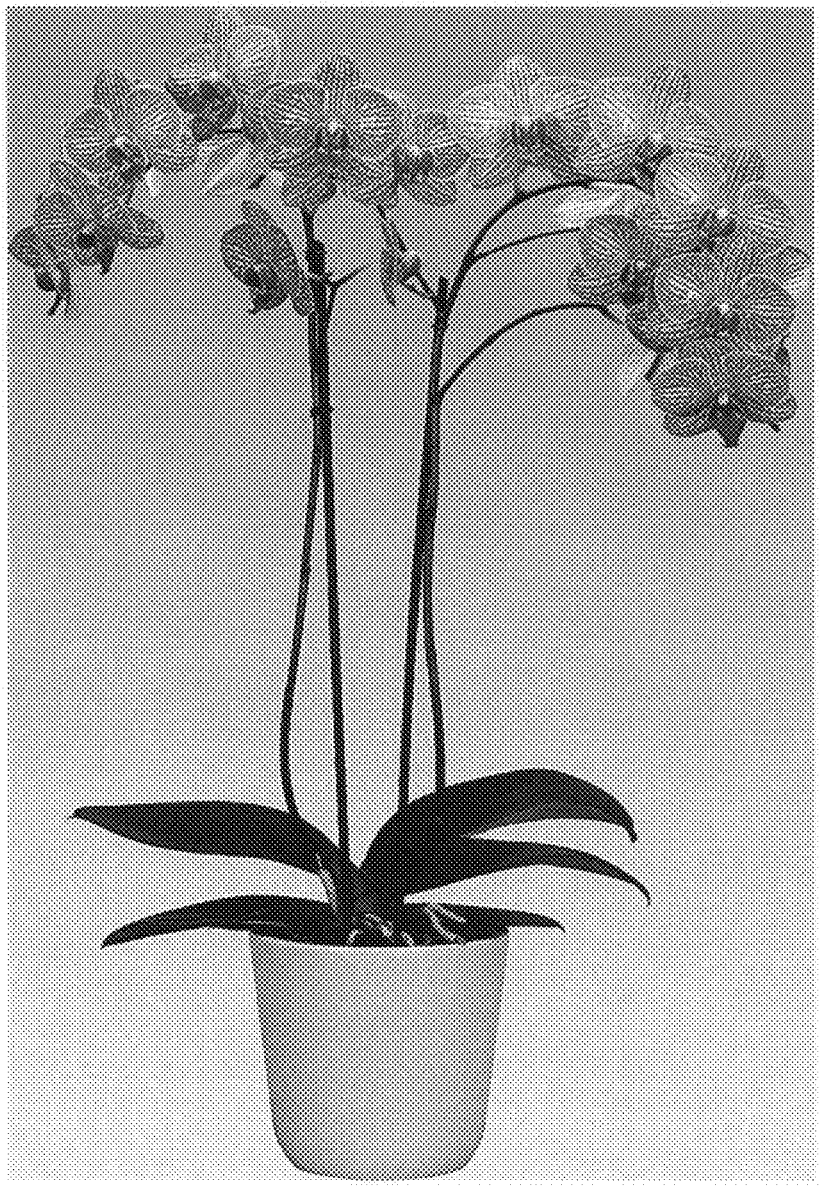
FIG. 1 shows a side view perspective of a typical flowering plant of 'Miraculous' in a 12 cm pot, at 16 months of age.

The new *Phalaenopsis* cultivar 'Miraculous' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Miraculous' as grown in a greenhouse in Strengweg, Heemskerk, The Netherlands, under conditions which closely approximate those generally used in commercial practice. Initially, the ideal temperature to grow plants of 'Miraculous' is 27° C. during the day and at night. Then, during the flowering phase of 'Miraculous', the ideal growing temperature is 20-22° C. during the day and 18° C. at night. Light levels for growing 'Miraculous' are a minimum of 5,000 lux and a maximum of 10,000 lux. A balanced fertilizer with level of 200 ppm N, 87 ppm P, 168 ppm K is applied. Duration of growth of 'Miraculous' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'Miraculous' plants described is 12 months after potting.

Classification:

*Botanical.*—*Phalaenopsis* hybrid.

Parentage:

*Female or seed parent.*—*Phalaenopsis* cultivar designated 'Sun Prince', unpatented.

*Male or pollen parent.*—*Phalaenopsis* cultivar designated 'Super Stupid', unpatented.

Propagation:

*Type.*—Tissue culture.

*Rooting habit and description.*—Fleshy; approximately 4 mm-7 mm wide and green in color (RHS 137A); freely branching. It takes 12 weeks for plants growing in tissue culture to initiate roots.

Plant:

*Size at maturity.*—Height (from bottom of pot to highest flower): about 63 to 68 cm. Spread: about 43 to 60 cm.

*Growth habit.*—Standard; yellow/green (RHS 147A) leaves and relatively normal raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19° C. about 2 racemes with flowers appear.

Foliage:

*Quantity per plant.*—About 6 to 8 leaves are produced before flowering.

*Arrangement and attachment.*—Half up/horizontal and on two sides.

*Overall shape of leaf.*—Oval, tip is blunt and asymmetric.

*Texture* (*both surfaces*).—Smooth and leathery.

*Pubescence.*—None.

*Leaf base.*—Acute.

*Margin.*—Entire.

*Mature leaf length.*—About 14 to 19 cm.

*Mature leaf width.*—About 9 to 12 cm.

*Mature leaf thickness.*—About 1 to 2 mm.

*Mature leaf color* (*upper surface*).—Yellow/green (RHS 147A).

*Mature leaf color* (*under surface*).—Yellow/green (RHS 146B).

*Venation.*—Pattern: parallel. Color of midvein: upper surface: yellow/green (RHS 147A). under surface: yellow/green (RHS 146A).

Raceme:

*Quantity per plant.*—About 1 to 3.

*Number of flowers per raceme.*—About 6 to 17.

*Length.*—About 54 to 68 cm.

*Diameter.*—About 3 to 5 mm.

*Strength.*—Strong.

*Aspect.*—Upright.

*Texture.*—Glabrous and smooth.

*Color.*—Green (RHS N137C).

*Internode.*—Length: about 27 to 50 mm.

Inflorescence description:

*Appearance*.—Upright to slightly pendant, racemose inflorescence with bilaterally symmetrical flowers that open in succession beginning with the lowermost flower.

*Buds*.—Height (from base to tip): about 15 mm to 25 mm. Diameter (at midpoint): about 10 mm to 20 mm. Shape: oval/egg-shaped. Color: yellow/green (RHS 145B).

*Flowering time*.—For an untreated plant (flowering plant that has not undergone cold-treatment where the plant grows at a temperature of 18° C. to 19° C. for about 4 to 8 weeks after a period of about 30 weeks at a temperature of 25° C.), 2 racemes appear with about 16 to 20 flower buds and flowers per inflorescence. First flowers can be expected approximately 4 to 6 months after planting a plant with a leaf diameter of 3 to 5 cm. Flowers persistent.

*Flowering longevity*.—On the plant: about 4 to 6 months; lastingness of cut flowers: has not been observed.

*Fragrance*.—Fragrance.

Figure 2:
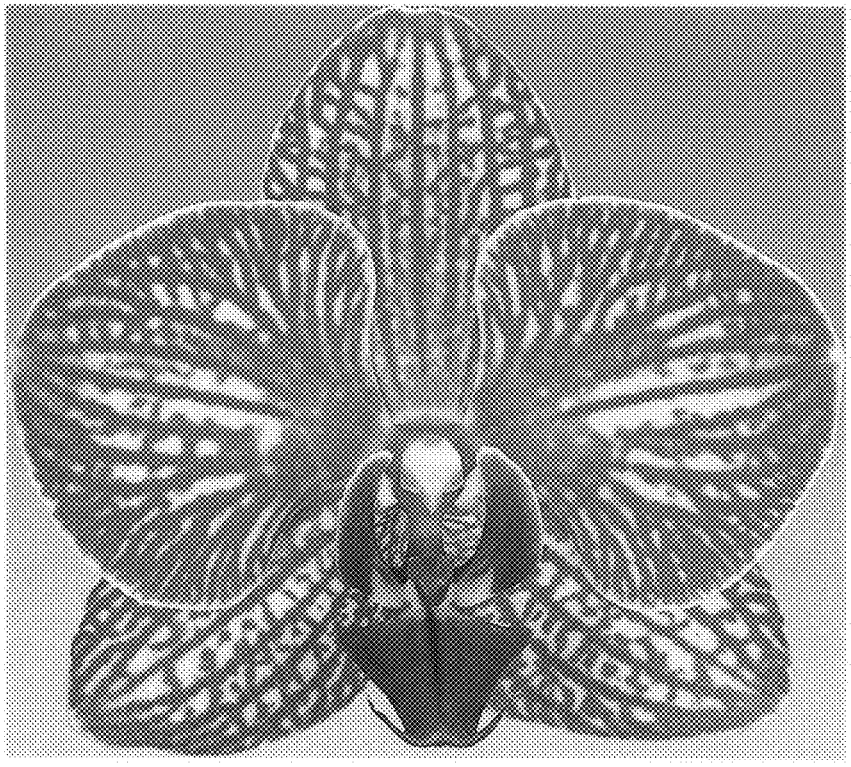
FIG. 2 shows a close-up view of a typical flower of 'Miraculous'.
Figure 3:
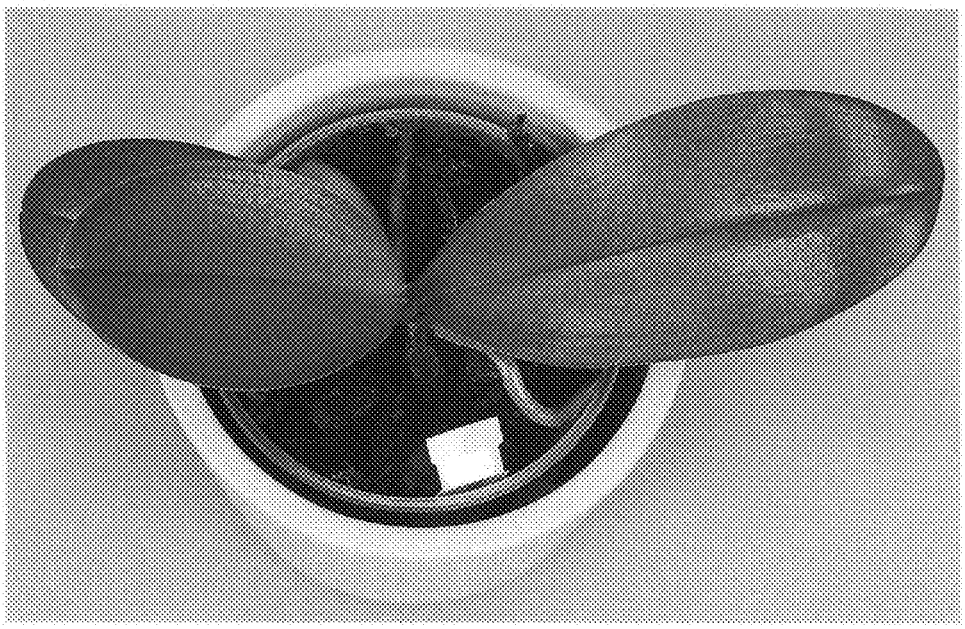
FIG. 3 shows a close-up view of the typical leaves of 'Miraculous'

*Flower*.—Rate of opening: Flowers fully opened about 2 to 3 days after petal and sepal separation. Orientation at opening: slanted upward and outward. Shape: typical shape of *Phalaenopsis* orchid; see FIG. 2. Size (of single bloom): Height: about 50 mm. Diameter: about 60 mm. Depth of tube: about 10 mm.

*Petals*.—Quantity and arrangement: three petals and three sepals that are trimerous, overlapping and arranged in 2 whorls. Petals are more pronounced than sepals. Arrangement: Inner whorl comprises 3 petals: 2 lateral petals and labellum. 2 lateral petals: Overall shape: broadly ovate, little bit triangular and weakly cupped. Apex: oval. Margin: entire and weakly undulate. Base: broadly ovate. Length: about 30 mm. Width: about 26 mm. Texture: Upper surface: smooth and satiny. Under surface: smooth and satiny. Color (when fully opened): upper surface: main color and edge are white (RHS N155D), stripes are red/purple (RHS 72A), spots and outer edges are red/purple (RHS 72B). Under surface: at the base is RHS N47B, main color is white (RHS N155D), stripes are purple (RHS 77A). Labellum: Overall shape: 3-lobed with 2 prominent callosities at central junction of the lateral lobes and base of the midlobe. Lateral lobes of labellum fold upward about the column; the midlobe extends forward and is terminated by 2 filiform appendages at the apex. Lateral lobes of the labellum are ovate in shape while the midlobe is triangular with a bump and a rib on it. Margin: entire and weakly undulate. Apex: oval. Length: about 16 mm. Width (not flattened): about 16 mm. Texture: Upper & under surface: smooth and satiny. Color (when fully opened): Mid lobe, upper surface: purple (RHS N79C) with a purple line in the center (RHS N79B). Under surface is purple (RHS 77B) at the base and in the center. Main color is purple (RHS N79C). Lateral lobes, upper surface: at the base yellow (RHS 6B) and white (RHS NN155D) and purple (N79C) which turns into purple (RHS N81B). Edges are yellow (RHS 6B) and white (RHS NN155D). Under surface: white (RHS N155B) and purple (RHS N81A) at the base. Edges are yellow (RHS 6B) and white (RHS NN155D). Main color is purple (RHS N81B). Cirrhi: short. Color: purple (RHS N79C) with white tips (RHS NN155D). Pestle (Callosities): Length: About 3 mm. Width (not flattened): about 3 mm. Color: at the base white (RHS NN155D), on top and on front and back red/purple (RHS 61A) and grey/orange (RHS 163A).

*Sepals*.—Arrangement: Outer whorl comprises 3 sepals. Overall shape: elliptical and weakly cupped. Margin: entire and weakly undulate. Length: about 30 to 35 mm. Width: about 25 to 30 mm. Apex: oval; dorsal sepal has a small notch. Texture: Upper & under surface: smooth and satiny. Color (when fully opened): Dorsal sepal: main color and edges are white (RHS N155D), stripes/spots are red/purple (RHS 72A), base and spots are red/purple (RHS 72B). Under surface: main color and edges are white (RHS N155D), stripes/spots are purple (RHS 77A). Lateral sepal: main color and edges are white (RHS N155D). Stripes and spots are red/purple (RHS 72A). The base and some spots are purple (RHS 72B). Under surface: main color and edges are white (RHS N155C), spots and stripes are purple (RHS 77A).

*Pedicel*.—Length: about 36 mm. Diameter: about 3 mm. Texture: glabrous and smooth. Color: at the base green (RHS N137A) in the middle yellow/green (RHS 146B) at the end white (RHS N155C).

Reproductive organs:

*Arrangement*.—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

*Column*.—Length: about 7 mm. Diameter: about 6 mm. Color: Main color purple (RHS 77B), at the base red/purple (RHS 78A) and the tip and edges white (RHS N155C).

*Pollinia*.—Quantity: Two. Size: about 1 mm. Color: yellow/orange (RHS 23A).

*Ovary*.—Length: about 4 mm. Diameter: about 5 mm. Color: purple (RHS 76D).

Disease/pest resistance/susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'Miraculous', as illustrated and described herein.

* * * * *